United States Patent
Sakai et al.

(10) Patent No.: US 6,889,536 B2
(45) Date of Patent: May 10, 2005

(54) AIR/FUEL-RATIO DETECTING APPARATUS

(75) Inventors: Shoichi Sakai, Gunma (JP); Futoshi Ichiyanagi, Gunma (JP)

(73) Assignee: Hitachi, Ltd., Kanagawa (JP)

( * ) Notice: Subject to any disclaimer, the term of this patent is extended or adjusted under 35 U.S.C. 154(b) by 5 days.

(21) Appl. No.: 10/702,768

(22) Filed: Nov. 7, 2003

(65) Prior Publication Data

US 2004/0099053 A1 May 27, 2004

(30) Foreign Application Priority Data

Nov. 18, 2002 (JP) ........................................ 2002-333901

(51) Int. Cl.⁷ ............................................. G01N 27/407
(52) U.S. Cl. ..................... 73/23.32; 73/118.1
(58) Field of Search ............................ 73/23.31, 23.32, 73/116, 117.2, 117.3, 118.1

(56) References Cited

U.S. PATENT DOCUMENTS

| | | | | | |
|---|---|---|---|---|---|
| 5,686,654 A | * | 11/1997 | Friese et al. | ............... | 73/23.32 |
| 5,804,699 A | * | 9/1998 | Sugiyama et al. | ......... | 73/23.32 |
| 5,811,660 A | * | 9/1998 | Nakano et al. | ............ | 73/23.32 |
| 6,332,966 B1 | * | 12/2001 | Sakai et al. | .................. | 204/425 |
| 6,354,134 B1 | * | 3/2002 | Katafuchi et al. | ......... | 73/23.32 |
| 6,367,309 B1 | * | 4/2002 | Diehl et al. | ................ | 73/23.32 |
| 6,442,998 B2 | * | 9/2002 | Kurokawa et al. | ......... | 73/31.05 |
| 6,571,602 B2 | * | 6/2003 | Ohkuma | .................... | 73/23.32 |
| 6,651,639 B2 | * | 11/2003 | Hada et al. | ................. | 123/697 |
| 2003/0052004 A1 | * | 3/2003 | Isitani et al. | ................ | 204/424 |
| 2003/0188967 A1 | * | 10/2003 | Isitani et al. | ................ | 204/406 |

FOREIGN PATENT DOCUMENTS

JP          61-100651 A          5/1986

* cited by examiner

*Primary Examiner*—Eric S. McCall
(74) *Attorney, Agent, or Firm*—Sughrue Mion, PLLC

(57) ABSTRACT

An air/fuel-ratio detecting apparatus includes a compact layer arranged on the outer surface of a solid electrolyte layer to externally conceal a gas diffusion layer, solid electrolyte layer, outer measuring electrode, and reference electrode to restrain entry of exhaust gas. A gas introduction window is formed in the compact layer to have a predetermined width. The gas introduction window allows entry of exhaust gas toward the gas diffusion layer and the outer measuring electrode in the range of an opening width of the gas introduction window.

13 Claims, 10 Drawing Sheets

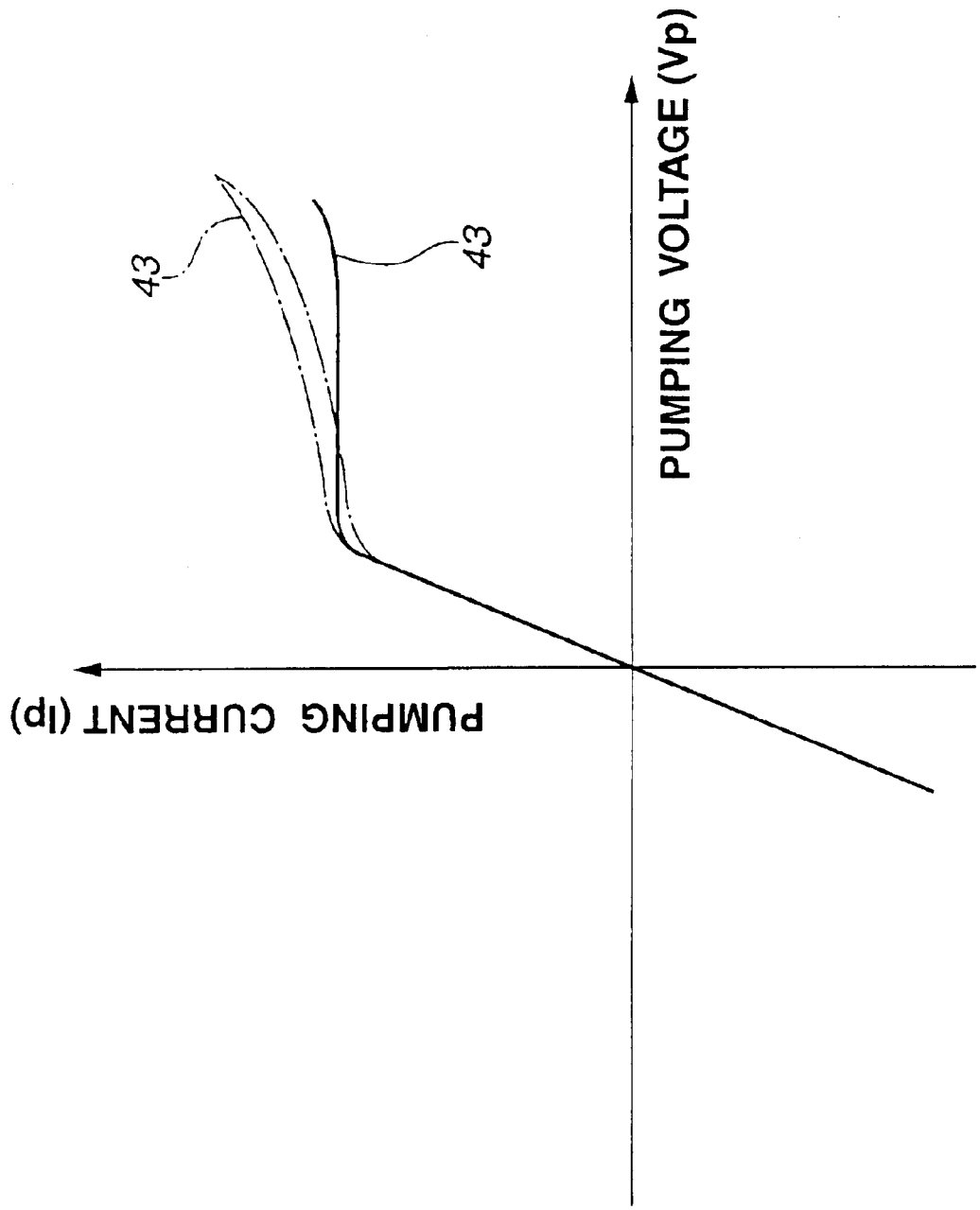

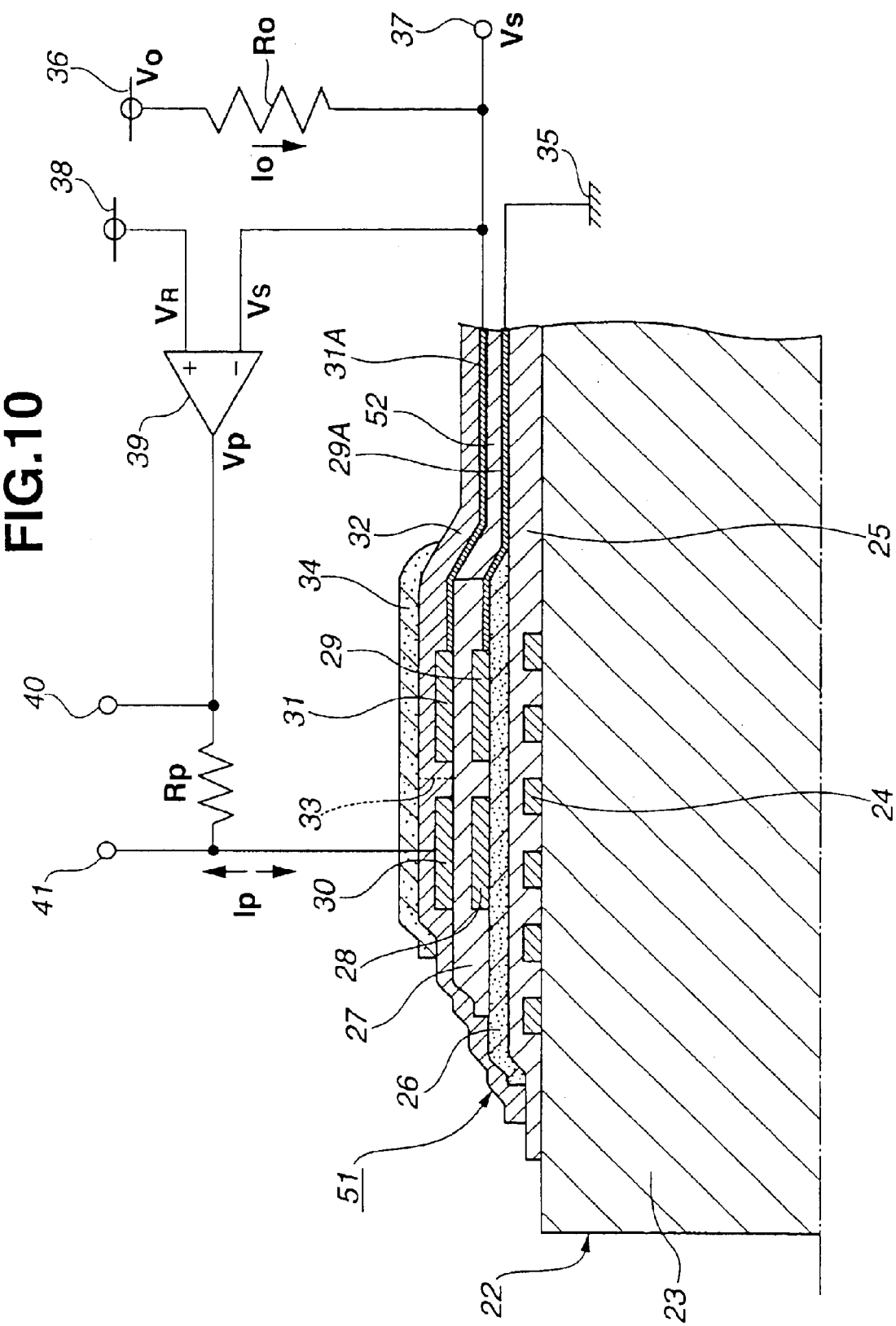

AIR/FUEL-RATIO DETECTING APPARATUS

BACKGROUND OF THE INVENTION

The present invention relates to an apparatus for detecting an air/fuel ratio of engines such as an automotive engine.

Typically, automotive engines include an air/fuel-ratio sensor (including an oxygen sensor) arranged in an exhaust pipe or the like and for detecting the oxygen concentration or the like in exhaust gas.

The air/fuel-ratio sensor comprises typically an elongate plate-like heater, an oxygen-ion conductive solid electrolyte layer formed on the heater in a laminated way and activated by heat therefrom, a plurality of electrodes arranged on the surface of the electrolyte layer, and a gas diffusion layer which cooperates with the electrolyte layer to externally cover the electrodes.

The air/fuel-ratio sensor detects an engine air/fuel ratio by measuring pumping current or diffusion limiting current which passes between the electrodes when externally applying the voltage to the air/fuel-ratio sensor.

Using an air/fuel-ratio detection signal derived from the air-fuel-ratio sensor, an engine electronic control unit feedback-controls a fuel-injection amount in such a way as to bring the air/fuel ratio close to a theoretical value (A/F= 14.7), a lean value (A/F≧15), and the like, thereby enhancing the combustion efficiency and fuel consumption of the engine.

SUMMARY OF THE INVENTION

With the above air/fuel-ratio sensor, however, since the electrodes arranged on the surface of the solid electrolyte layer are simply covered with the gas diffusion layer made of a porous material, a plurality of paths run in various directions, which allow gas to be measured such as exhaust gas to reach the electrodes through the gas diffusion layer.

This raises easy occurrence of variations in gas diffusion resistance produced when exhaust gas reaches the electrodes through the gas diffusion layer, rendering the characteristic of diffusion limiting current unstable, leading to a reduction in detection accuracy of the air/fuel ratio.

It is, therefore, an object of the present invention to provide an air/fuel ratio detecting apparatus which contributes to stability of the characteristic of diffusion limiting current and thus enhancement in detection accuracy of the air/fuel ratio.

The present invention provides generally an apparatus for detecting an air/fuel ratio, which comprises: a heater which generates heat through outside energization; a gas diffusion layer provided to the heater, the gas diffusion layer allowing a gas to be measured to diffuse therein; a solid electrolyte layer provided to the heater outside the gas diffusion layer, the solid electrolyte layer being activated by heat of the heater, the solid electrolyte layer being oxygen-ion conductive; a first electrode arranged between the gas diffusion layer and the solid electrolyte layer, the first electrode being exposed to the gas passing through the gas diffusion layer; a second electrode arranged on an outer surface of the solid electrolyte layer, the second electrode facing the first electrode across the solid electrolyte layer, the second electrode and the first electrode allowing a pumping current to flow therebetween when externally applying voltage thereto; a third electrode arranged on the outer surface of the solid electrolyte layer away from the second electrode, the third electrode and the first electrode allowing an electromotive force corresponding to an oxygen concentration in the gas to be generated therebetween; a first compact layer arranged on the outer surface of the solid electrolyte layer, the first compact layer concealing externally the gas diffusion layer, the solid electrolyte layer, the second electrode, and the third electrode to restrain entry of the gas; and an opening formed in the first compact layer, the opening having a predetermined width, the opening allowing entry of the gas toward the gas diffusion layer and the second electrode in a range of the width.

BRIEF DESCRIPTION OF THE DRAWINGS

The other objects and features of the present invention will become apparent from the following description with reference to the accompanying drawings, wherein:

FIG. 9 is a graph similar to FIG. 8, illustrating the relationship between the pumping voltage and the pumping current, which serve to detect the air/fuel ratio; and FIG. 10 is a diagram similar to FIG. 7, showing a second embodiment of the present invention.

DETAILED DESCRIPTION OF THE INVENTION

Figure 1:
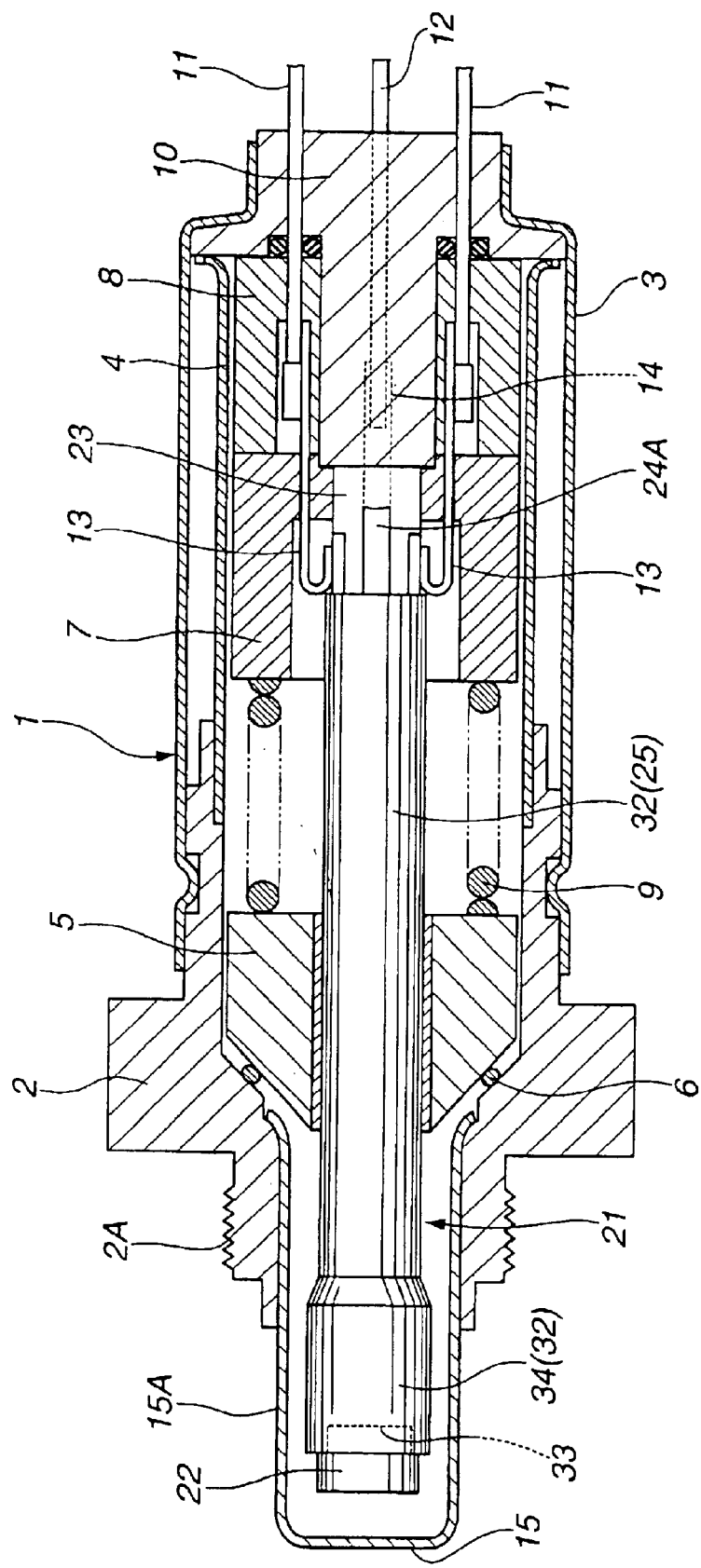
FIG. 1 is a longitudinal sectional view showing a first embodiment of an air/fuel-ratio sensor including an air/fuel-ratio detecting element or device according to the present invention.

Referring to the drawings wherein like reference numerals designate like parts throughout the views, an air/fuel-ratio detecting apparatus embodying the present invention will be described. In the illustrative embodiments, the air/fuel-ratio detecting apparatus is applied to a wide-area air/fuel-ratio sensor mounted to an exhaust pipe of an automotive engine.

Referring to FIGS. 1–9, there is shown first embodiment of the present invention. Referring to FIG. 1, the air/fuel-ratio sensor comprises a casing 1 comprising a stepped cylindrical holder 2 having an external thread or mounting portion 2A formed on the outer periphery of one axial end or front end, a bottomed cylindrical cap 3 integrally secured to another axial end or base end of holder 2, and a guide tube 4 disposed coaxially in cap 3 and positioned between holder 2 and a seal cap 10 as will be described later.

Holder 2, cap 3, and guide tube 4 constituting casing 1 are made of a metallic material such as stainless steel. In order to protrusively arrange in the exhaust pipe, not shown, an air/fuel-ratio detecting element or device 21 as will be described later, casing 1 has external thread 2A engaged with the exhaust pipe.

An insulating support 5 is disposed in holder 2 of casing 1 through a metallic seal ring 6. Insulating support 5 is formed cylindrically out of a ceramic material such as aluminum oxide or alumina ($Al_2O_3$), and has an inner periphery to which air/fuel-ratio detecting element 21 is fixed. Insulating support 5 serves to position air/fuel-ratio detecting element 21 in casing 1, and hold it in the electrically thermally insulated state.

Insulating cylinders 7,8 are disposed in guide tube 4 of casing 1. Insulating cylinders 7, 8 are made of a ceramic material such as alumina to insulatedly hold contact plates 13, 14 and the like as will be described later with respect to casing 1.

A spring or elastic member 9 is disposed in casing 1 between insulating support 5 and insulating cylinder 7. Spring 9 serves to always bias insulating support 5 toward holder 2 to prevent vibration, impact, and the like which may externally act on casing 1 from being transmitted directly to air/fuel-ratio detecting element 21.

A seal cap 10 is arranged to close a base end of cap 3. Seal cap 10 is formed like a stepped cylinder out of a heat-resistant resin material or the like. Seal cap 10 serves to position insulating cylinders 7, 8 and the like in casing 1 through spring 9.

Arranged through seal cap 10 are detection-use lead wires 11, 11, . . . and heater-use lead wires 12, 12 (only one of which is shown in FIG. 1). Lead wires 11,12 are electrically connected to detection-use contact plates 13, 13, . . . and heater-use contact plates 14, 14, respectively A protector 15 is provided to holder 2 of casing 1, and is formed like a lidded cylinder out of a metallic plate of high heat resistance or the like. Protector 15 has a base end mounted to holder 2 in such a way as to externally conceal a front end of air/fuel-ratio detecting element 21, and a front end or lid protruding axially from holder 2.

Formed with protector 15 in its cylindrical portion are a plurality of windows 15A, 15A, . . . which allow circulation of exhaust gas or gas to be measured. Windows 15A serve to guide exhaust gas which flows through the exhaust pipe to the vicinity of a front end of air/fuel-ratio detecting element 21.

Air/fuel-ratio detecting element 21 serving as an air/fuel-ratio detecting apparatus is arranged in holder 2 of casing 1 through insulating support 5 to have the front end protruding axially from holder 2. Referring to FIGS. 2–7, air/fuel-ratio detecting element 21 comprises a heater 22, a gas diffusion layer 26, a solid electrolyte layer 27, a compact layer or first compact layer 32, and a protecting layer 34 as will be described later.

Figure 2:
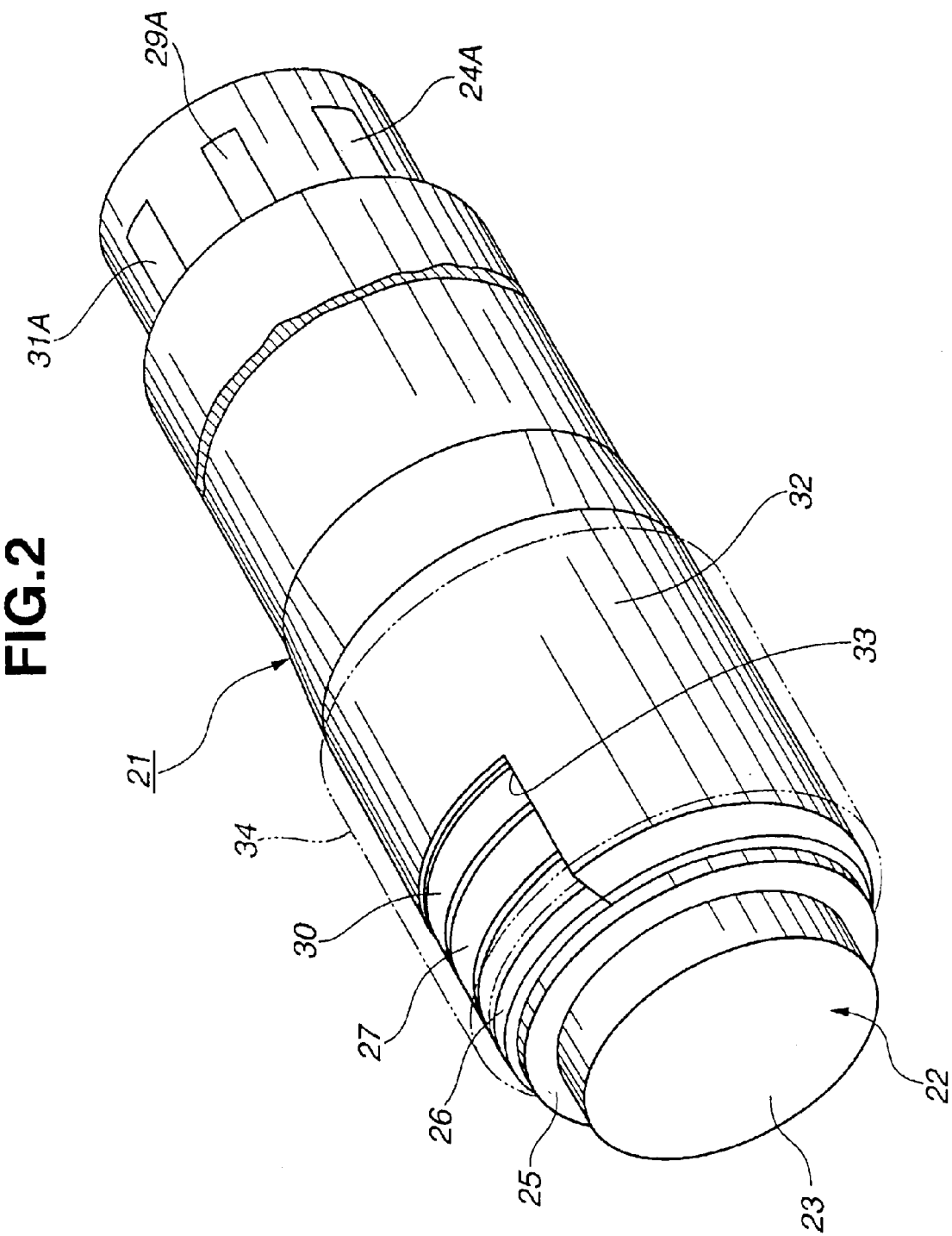
FIG. 2 is an exploded perspective view showing the air/fuel-ratio detecting element in FIG. 1.
Figure 3:
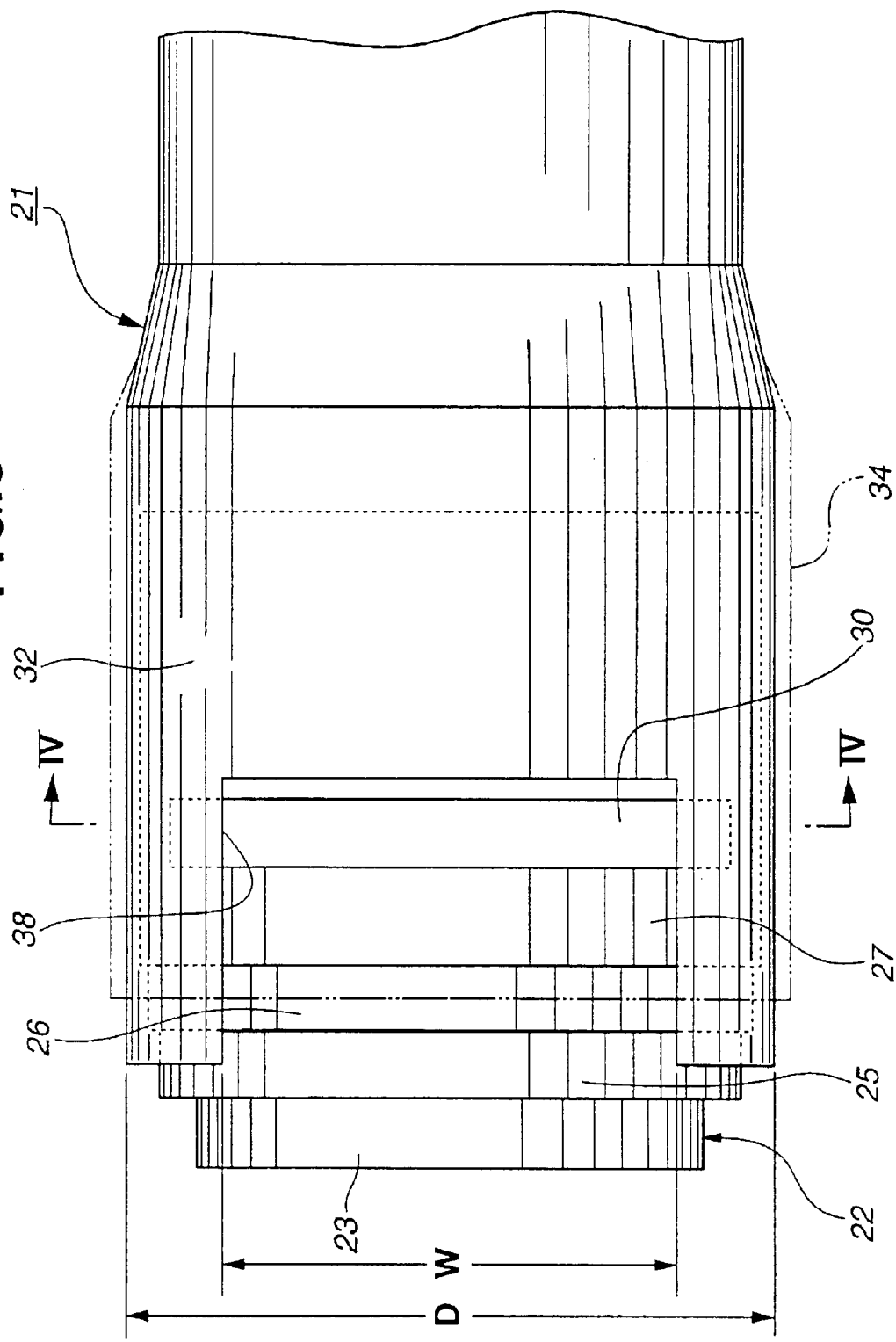
FIG. 3 is a plan view showing the air/fuel-ratio detecting element in FIG. 2.
Figure 4:
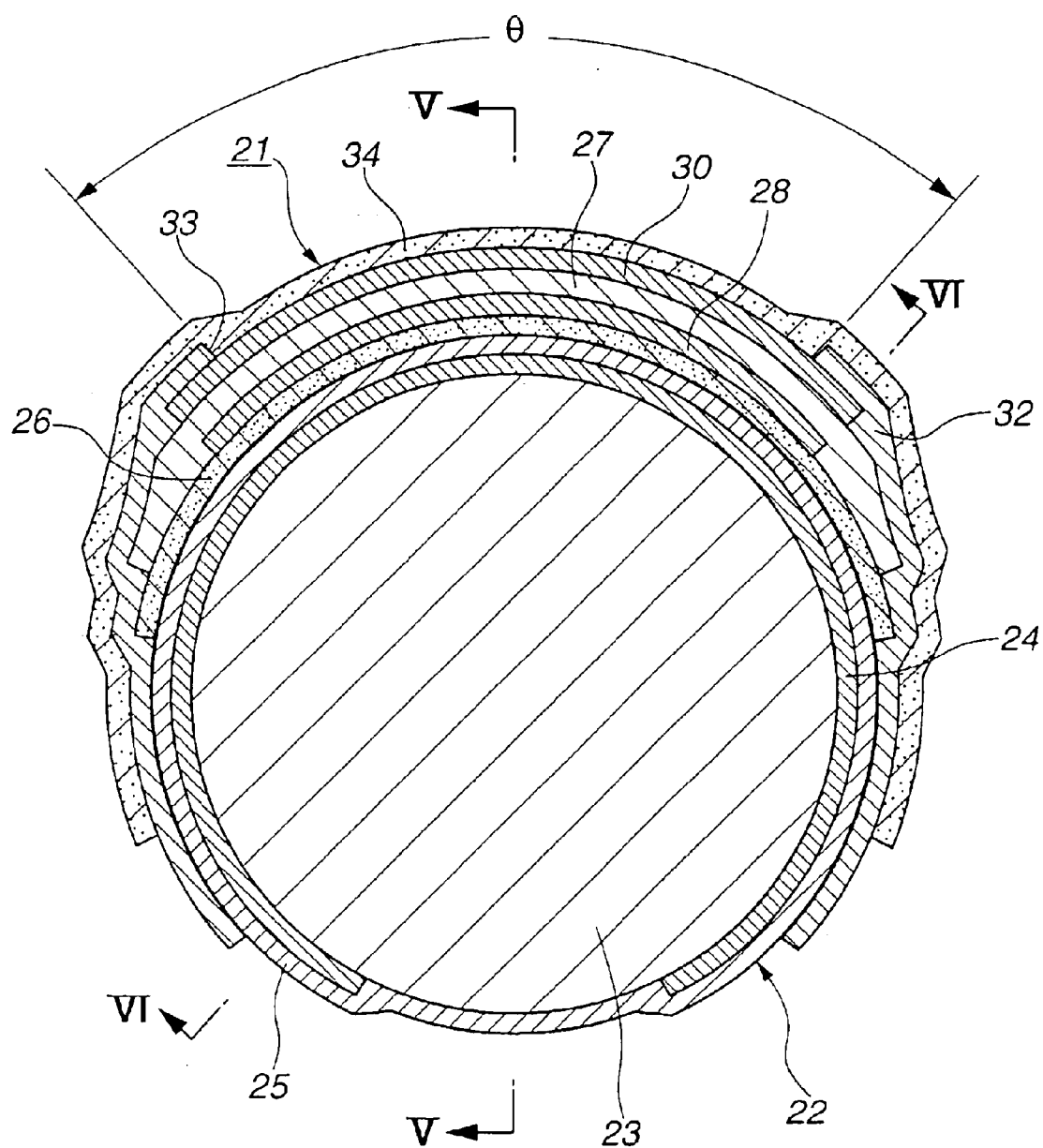
FIG. 4 is a sectional view taken along the line IV—IV in FIG. 3.

Referring to FIGS. 2–4, heater or stem 22 is shaped like an elongate rod, and comprises a small-diameter heater core 23 formed like a solid rod out of a ceramic material such as alumina, a heater pattern 24, and an insulative heater covering layer 25.

Figure 5:
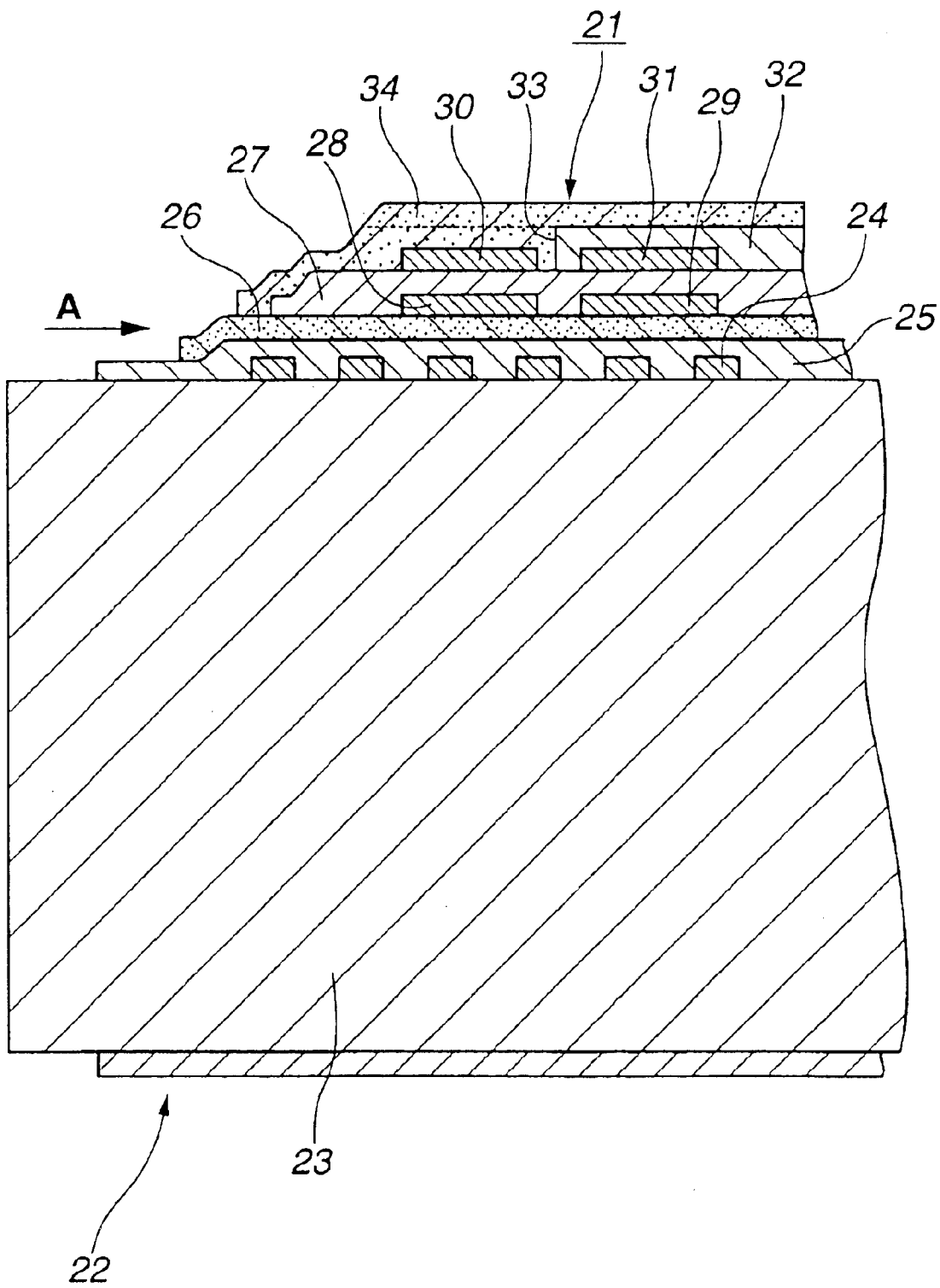
FIG. 5 is a view similar to FIG. 4, taken along the line V—V in FIG. 4.

As best seen, e.g. in FIG. 5, heater pattern 24 is made of a heat-generating conductor material such as platinum containing alumina, and is arranged on the peripheral surface of heater core 23 through curved-surface printing or the like. Heater pattern 24 includes a pair of lead portions 24A, 24A (only one of which is shown in FIG. 2) extending from a front end to a base end of heater core 23. As shown in FIG. 1, lead portions 24A are connected to heater-use contact plates 14 at the base end of heater core 23.

Heater pattern 24 is supplied with power from an external heater power source, not shown, through heater-use lead wires 12, contact plates 14, and lead portions 24A to heat heater 22 to the temperature of, e.g. about 650–800° C.

In order to radially externally protect heater pattern 24 together with lead portions 24A, heater covering layer 25 is arranged on the periphery of heater core 23 by thick-film printing a ceramic material such as alumina through curved-surface printing or the like. Gas diffusion layer 26 and the like are arranged on the outer periphery of heater covering layer 25 in a laminated way through curved-surface printing or the like.

Referring to FIGS. 4–7, gas diffusion layer 26 is arranged on the outer periphery of heater covering layer 25 of heater 22 by thick-film printing a paste comprising, e.g. alumina powder (which may contain a predetermined weight percent of zirconic powder) through curved-surface printing or the like.

Gas diffusion layer 26 is of the porous structure having vacant holes in the form of continuous bubbles. While diffusing part of exhaust gas which flows along the perimeter of air/fuel-ratio detecting element 21 inside gas diffusion layer 26 through a gas introduction window 33 as will be described later from the direction of arrow A in FIG. 5 or axial direction, gas diffusion layer 26 allows exhaust gas to pass toward an inner electrode 28 as will be described later.

Oxygen-ion conductive solid electrolyte layer 27 is arranged on the outer periphery of heater covering layer 25 through curved-surface printing or the like. Specifically, referring to FIGS. 4–7, solid electrolyte layer 27 is formed annularly by thick-film printing a paste containing, e.g. yttria-stabilized zirconia (YSZ) on the periphery of heater covering layer 25 from the outside of gas diffusion layer 26.

Solid electrolyte layer 27 has a function of transporting oxygen ions and the like between electrodes 28, 29 and between electrodes 28, 31 as will be described later. Solid electrolyte layer 27 is of the compact structure roughly similar to that of compact layer 32 as will be described later so as to prevent penetration or entry of exhaust gas or the like.

As shown in FIG. 4, solid electrolyte layer 27 is arranged on the outer periphery of heater covering layer 25 and on the gas diffusion layer 26 in a laminated way. Solid electrolyte layer 27 is smaller in circumferential length than gas diffusion layer 26. As a result, gas diffusion layer 26 is not externally totally concealed with solid electrolyte layer 27, and thus has both circumferential sides protruding therefrom in the circumferential direction of heater covering layer 25 as shown in FIG. 4.

Inner electrodes or first electrodes 28, 29 are arranged on the inner periphery of solid electrolyte layer 27 between gas diffusion layer 26 and solid electrolyte layer 27. Referring to FIGS. 4–7, inner electrodes 28, 29 are made of a conductive material such as platinum, and are formed on the outer periphery of gas diffusion layer 26 through curved-surface printing or the like before curved-surface printing of solid electrolyte layer 27.

Figure 6:
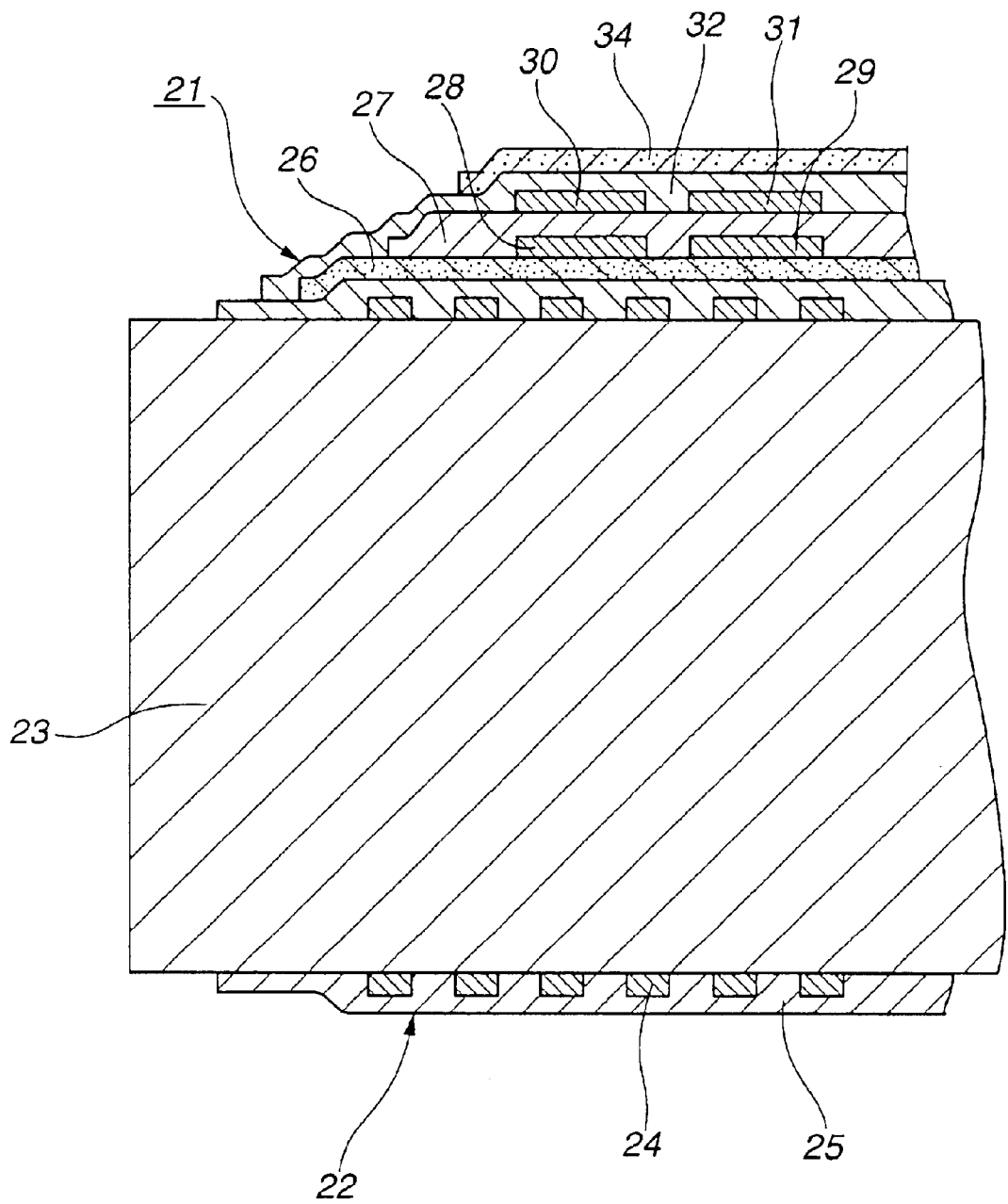
FIG. 6 is a view similar to FIG. 5, taken along the line IV—IV in FIG. 4.
Figure 7:
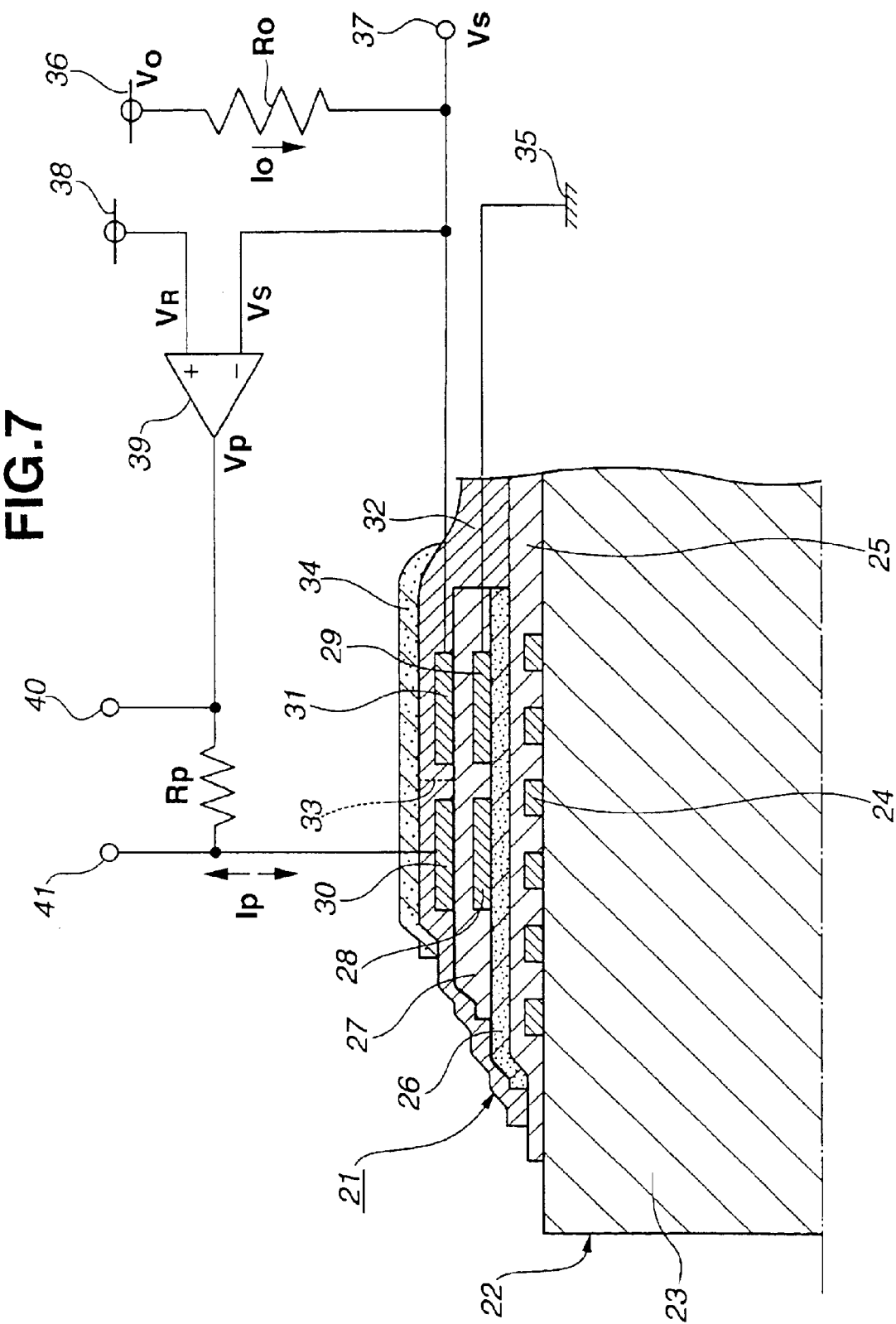
FIG. 7 is a diagram showing a circuit for the air/fuel-ratio detecting element.

Referring to FIGS. 5–7, inner electrodes 28, 29 are disposed away from each other in the axial direction of gas diffusion layer 26, and opposite to electrodes 30, 31 as will be described later in the radial direction of gas diffusion layer 26 across solid electrolyte layer 27. Inner electrodes 28, 29 are connected to each other through lead wires or the like, not shown, to be at the same potential as that of a virtual ground 35 as shown in FIG. 7 and as will be described later.

As seen in FIG. 2, inner electrodes 28, 29 include a lead portion or wire 29A on the side of inner electrode 29, for example, which extends in the axial direction of heater covering layer 25 toward a base end of heater 22. Solid electrolyte layer 27 is curved-surface printed on the outer peripheral surface of heater covering layer 25 in such a way as to externally totally envelop inner electrodes 28, 29 except lead portion 29A.

An outer measuring electrode or second electrode 30 is arranged on the peripheral surface of solid electrolyte layer 27 close to a front end of heater 22. Referring to FIGS. 4–7, outer measuring electrode 30 is disposed to face inner electrode 28 across solid electrolyte layer 27. Inner electrode 28 and outer measuring electrode 30 form a pumping electrode so called.

Outer measuring electrode 30 includes a lead portion or wire, not shown, similar to a lead portion 31A of a reference electrode 31 as will be described later. The lead portion is formed away from lead portion 31A of reference electrode 31 in the circumferential direction of heater covering layer 25 and extending axially to the base end of heater 22 along heater covering layer 25.

Reference electrode or third electrode 31 is arranged on the outer peripheral surface of solid electrolyte layer 27 away from outer measuring electrode 30 in the axial direction of heater 22. Referring to FIGS. 5–7, reference electrode 31 is disposed to face inner electrode 29 across solid electrolyte layer 27, so that an electromotive force corresponding to the concentration oxygen in exhaust gas is generated between two electrodes 29, 31 as will be described later.

Outer measuring electrode 30 and reference electrode 31 are made of the same conductive material as that of inner electrodes 28, 29, and are formed by curved-surface printing a conductive-material paste on the outer peripheral surface of solid electrolyte layer 27. As shown in FIG. 2, reference electrode 31 includes lead portion or wire 31A extending toward the base end of heater 22.

Lead portion 29A of inner electrodes 28, 29, lead portion of outer measuring electrode 30, and lead portion 31A of reference electrode 31 are connected to contact plates 13 and lead wires 11 on the base-end side of air/fuel-ratio detecting element 21 as shown in FIG. 1, providing an electric circuit as shown in FIG. 7.

Compact layer 32 is arranged to externally conceal gas diffusion layer 26, solid electrolyte layer 27, electrodes 30, 31, and the like. Compact layer 32 is formed by thick-film printing a paste comprising, e.g. alumina powder with silicon dioxide ($SiO_2$) added on the outer periphery of heater covering layer 25 from the outside of gas diffusion layer 26, solid electrolyte layer 27, and the like. As shown in FIG. 7, compact layer 32 extends from the front end to the base end of heater covering layer 25.

Since powder forming the paste is of small average grain diameter (about 0.3–0.5 μm, for example), compact layer 32 is more compact in structure than gas diffusion layer 26 and the like, preventing entry of exhaust gas. As a result, reference electrode 31, exclusive of lead portion 31A, is fully surrounded with solid electrolyte layer 27 and compact layer 32, and is thus maintained in isolation from outside exhaust gas.

Likewise, gas diffusion layer 26 and outer measuring electrode 30, exclusive of a position of gas introduction window 33, are surrounded with compact layer 32 as shown in FIGS. 2 and 3, which prevents entry of exhaust gas. With this, the direction or path of exhaust gas entering gas diffusion layer 26 is limited to the direction of arrow A in FIG. 5 or length direction of heater 22, gas diffusion layer 26, and the like.

Gas introduction window or opening 33 is arranged in compact layer 32. Referring to FIGS. 2–5, gas introduction window 33 is shaped like a rectangular opening by cutting in a C-shape an end of compact layer 32 close to the front end of heater 22. As shown in FIG. 3, the relationship between an opening width W of gas introduction window 33 and an outer diameter D of compact layer 32 is given, for example, by the following expression (1):

$$W = (2/3 \text{ to } 1) \times D \qquad (1)$$

Gas introduction window 33 is formed with an opening angle θ as shown in FIG. 4. The relationship between opening width W and opening angle θ in connection with outer diameter D of compact layer 32 is given by the following expression (2):

$$W = (\theta/360) \times D \times \pi \qquad (2)$$

By way of example, when outer diameter D of compact layer 32 is 3 mm, opening width W of gas introduction window 33 is, for example, about 0–3.0 mm, preferably, about 2.5–2.8 mm.

Gas introduction window 33 extends to a position of outer measuring electrode 30 in the length or axial direction of air/fuel-ratio detecting element 21 as shown in FIGS. 2 and 3 so as to partly bare electrode 30 together with gas diffusion layer 26 and solid electrolyte layer 27 from compact layer 32. Gas introduction window 33 allows outside exhaust gas to enter gas diffusion layer 26 and contact outer measuring electrode 30 in the range of opening window W.

It is noted that since the outer periphery of gas diffusion layer 26 is concealed radially externally with solid electrolyte layer 27 having compact structure roughly similar to that of compact layer 32, outside exhaust gas may not pass through solid electrolyte layer 27 to reach gas diffusion layer 26.

As a result, only a front end or one length-direction side of gas diffusion layer 26 can contact exhaust gas at the position of gas introduction window 33. Gas introduction window 33 serves to introduce outside exhaust gas into gas diffusion layer 26 in the length direction or direction of arrow A in FIG. 5, and restrict entry of exhaust gas thereinto in other directions.

Protecting layer 34 serves to externally conceal compact layer 32 together with gas introduction window 33. Protecting layer 34 is made of a porous material such as alumina, and is formed by curved-surface printing a paste comprising powder thereof as shown with imaginary line in FIGS. 2 and 3.

It is noted that though protecting layer 34 is shown with imaginary line in FIGS. 2 and 3 to clearly illustrate gas introduction window 33, protecting layer 34 is arranged actually as shown with solid line in FIGS. 4–7. Protecting layer 34 is of coarse porous structure having higher porosity than that of gas diffusion layer 26.

Protecting layer 34 has a function of externally concealing gas diffusion layer 26, solid electrolyte layer 27, outer measuring electrode 30, and the like exposed to outside through gas introduction window 33, protecting them from outside dust and the like. Part of exhaust gas flowing along the perimeter of protecting layer 34 pass through protecting layer 34 having higher porosity to move from the position of gas introduction window 33 to gas diffusion layer 26, outer measuring electrode 30, and the like.

Virtual ground 35 is connected to inner electrodes 28, 29 as shown in FIG. 7, and is put at a reference potential of, e.g. about 1.5V.

A DC power source or voltage applying means 36 is arranged to apply DC voltage. DC power source 36 is connected to reference electrode 31 through an adjusting resistance Ro as shown in FIG. 7. DC power source 36 applies a predetermined DC voltage or pseudo-reference-electrode pumping voltage Vo of, e.g. about 2–3V to reference electrode 31 through adjusting resistance Ro.

Figure 8:
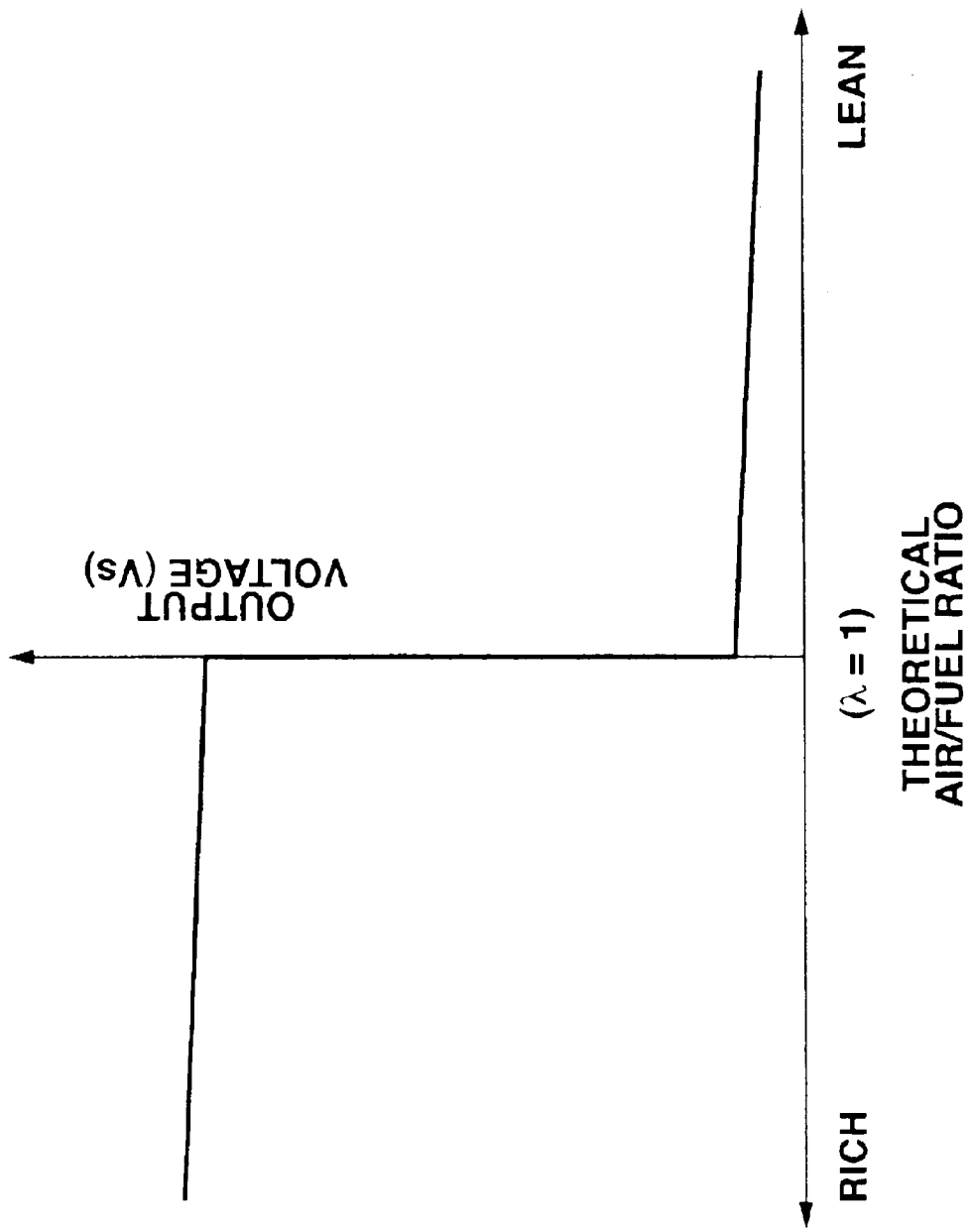
FIG. 8 is a graph illustrating the relationship between the output voltage of the air/fuel-ratio detecting element and the air/fuel ratio.

An output terminal 37 is arranged to provide a signal corresponding to the oxygen concentration in exhaust gas. Referring to FIG. 8, output terminal 37 provides an output voltage Vs as an oxygen-concentration detection signal as illustrated by a characteristic line, wherein output voltage Vs is given by the following expression (3):

$$Vs = E + (Ri \times Io) \qquad (3)$$

Specifically, solid electrolyte layer 27 of air/fuel-ratio detecting element 21 has an internal resistance Ri, and an electromotive force E corresponding to the oxygen concentration in exhaust gas is generated between inner electrode 29 and reference electrode 31 which face each other across solid electrolyte layer 27. And when supplying to electrodes 29, 31 with pumping current Io as an inflow current from DC power source 36, output voltage Vs is provided as an oxygen-concentration detection signal from output terminal 37.

A comparison power source 38 is arranged to set a comparison voltage VR. Comparison power source 38 serves to provide comparison voltage VR corresponding to a theoretical air/fuel ratio (A/F=14.7 or λ=1) to a differential amplifier 39 as will described later.

Differential amplifier 39 is arranged to provide an air/fuel-ratio signal between detection terminals 40, 41 as shown in FIG. 7. Differential amplifier 39 has a non-inverting input terminal connected to comparison power source 38 for comparison voltage VR and an inverting input terminal connected to output terminal 37 for output voltage Vs, i.e. reference electrode 31 of air/fuel-ratio detecting element 21.

Moreover, differential amplifier 39 has an output terminal connected to outer measuring electrode 30 through a detection resistance Rp. Arranged between detection terminals 40, 41 connected to respective ends of detection resistance Rp are a detector, not shown, for detecting a pumping current or diffusion limiting current Ip as an air/fuel-ratio signal and the like.

Differential amplifier 39 compares comparison voltage VR corresponding to theoretical air/fuel ratio with output voltage Vs, and provides to detection terminals 40, 41a signal indicative of a comparison result as a pumping voltage Vp. Then, pumping current Ip as an air/fuel-ratio signal flows between inner electrode 28 and outer measuring electrode 30. Referring to FIG. 9, the relationship between pump voltage Vp and pumping current Ip is shown, for example, by a characteristic curve 42.

Next, detecting operation of the air/fuel-ratio sensor will be described. Casing 1 of the air/fuel-ratio sensor is engaged with the exhaust pipe or the like through external thread 2A of holder 2, and is fixed thereto with the front end of air/fuel-ratio detecting element 21 protruding into the exhaust pipe.

When engine operation causes exhaust gas which flows through the exhaust pipe to reach the perimeter of air/fuel-ratio detecting element 21 through protector 15, part of this exhaust gas reaches both the surface of outer measuring electrode 30 through gas introduction window 33 of protecting layer 34 and compact layer 32, and the surface of inner electrodes 28, 29 through gas diffusion layer 26.

In this state, heater pattern 24 is supplied with power from the heater power source to heat air/fuel-ratio detecting element 21 in its entirety by heater 22, activating solid electrolyte layer 27. Voltage is applied from DC power source 36 between inner electrode 29 and reference electrode 31 which face each other across solid electrolyte layer 27, whereas voltage is applied through differential amplifier 39 between inner electrode 28 and outer measuring electrode 30 which also face each other across solid electrolyte layer 27.

With this, output voltage Vs and pumping voltage Vp corresponding to respective air/fuel ratio λ are generated across inner electrode 29 and reference electrode 31 and across inner electrode 28 and outer measuring electrode 30 in accordance with the oxygen concentration and flammable-gas component concentration in exhaust gas given by reaction formulas (I)–(VI) as will be described later. Then, pumping current Ip is provided as a detection signal between detection terminals 40, 41.

Specifically, at the lean air/fuel ratio wherein the actual air/fuel ratio is greater than the theoretical one, lean air/fuel mixture is formed in the engine combustion chamber. Due to this lean air/fuel mixture, certain oxygen remains in exhaust gas which flows along the perimeter of air/fuel-ratio detecting element 21 (protecting layer 34, for example). Along the direction of arrow A in FIG. 5, this oxygen in exhaust gas is delivered to inner electrodes 28, 29 through gas diffusion layer 26.

As a result, electrochemical decomposition reaction given by the following reaction formula (I) is produced between inner electrode 29 and reference electrode 31, for example, at electrode 29, by application of the voltage from DC power source 36. This adds electrons to oxygen molecules which remain in exhaust gas, generating oxygen ions.

$$O_2 + 4e \rightarrow 2O^{2-} \qquad (I)$$

where $O_2$ is oxygen molecule, e is electron, and $O^{2-}$ is oxygen ion.

Then, oxygen ions are transported from inner electrode 29 to reference electrode 31 through oxygen deficiency in solid electrolyte layer 27. Thus, electrochemical decomposition reaction given by the following reaction formula (II) is produced at reference electrode 31 to decompose oxygen ions into oxygen and electrons:

$$2O^{2-} \rightarrow O_2 + 4e \qquad (II)$$

where $O^{2-}$ is oxygen ion, $O_2$ is oxygen molecule, and e is electron.

Thus, oxygen is absorbed in reference electrode 31, for example, in its vacant holes, not shown, producing relatively high oxygen partial pressure in reference electrode 31. At the lean air/fuel ratio, however, oxygen is continuously delivered to inner electrode 29 through gas diffusion layer 26, so that inner electrode 29 is also put at high oxygen partial pressure, having a small difference in oxygen partial pressure between electrodes 29, 31.

As a result, electromotive force E shown in expression (3) and generated in solid electrolyte layer 27 in accordance with a difference in oxygen partial pressure between electrodes 29, 31 and the like is restrained to a small value. Thus, corresponding to the oxygen concentration in exhaust gas, the voltage of reference electrode 31, i.e. output voltage Vs of output terminal 37, has a lower value than that at the theoretical air/fuel ratio (λ=1) as shown by a characteristic line in FIG. 8.

On the other hand, at the rich air/fuel ratio wherein the actual air/fuel ratio is smaller than the theoretical one, due to excessively dense air/fuel mixture in the combustion chamber, no oxygen remains in exhaust gas which flows along the perimeter of protecting layer 34 and the like of air/fuel-ratio detecting element 21, and flammable-gas components such as carbon monoxide and hydrogen remain therein without being burned.

With this, no oxygen exists in exhaust gas delivered to inner electrodes 28, 29 through gas diffusion layer 26, leading to an abrupt drop in oxygen partial pressure in inner electrode 29, for example. Even in this state, however, oxygen is accumulated in the vacant holes of reference electrode 31, providing a large difference in oxygen partial pressure between electrodes 29, 31.

As a result, electromotive force E shown in expression (3) and generated in solid electrolyte layer 27 in accordance with a difference in oxygen partial pressure between electrodes 29, 31 and the like is increased largely. Thus, corresponding to the oxygen concentration in exhaust gas, the voltage of reference electrode 31, i.e. output voltage Vs of output terminal 37, has a higher value than that at the theoretical air/fuel ratio ($\lambda=1$) as shown by a characteristic lines in FIG. 8.

Since output voltage Vs of output terminal 37 varies largely corresponding to the oxygen concentration in exhaust gas as shown by the characteristic lines in FIG. 8, it can be determined whether the air/fuel ratio is in rich condition or in lean condition in accordance with output voltage Vs.

In this case, reference electrode 31 is connected to DC power source 36 as shown in FIG. 7, receiving DC voltage Vo for transporting oxygen ions from inner electrode 29 to reference electrode 31 through solid electrolyte layer 27.

As being fully surrounded with solid electrolyte layer 27 and compact layer 32, and is thus maintained in isolation from outside exhaust gas, reference electrode 31 can stably maintain the oxygen partial pressure at a higher value without being affected by variations in air/fuel ratio, allowing reference electrode 31 to perform pseudo function as an electrode of reference oxygen concentration or a reference electrode.

With this, output voltage Vs of output terminal 37, i.e. voltage of reference electrode 31, can provide a stable output characteristic wherein it is switched in an on-off way in accordance with whether the air/fuel ratio is in rich condition or in lean condition as shown by the characteristic lines in FIG. 8, resulting in accurate detection of the oxygen concentration in exhaust gas.

Moreover, the voltage of reference electrode 31, i.e. output voltage Vs of output terminal 37, is provided to differential amplifier 39 as shown in FIG. 7 to compare with comparison voltage VR corresponding to the theoretical air/fuel ratio. When the air/fuel ratio is in rich condition, output voltage Vs has a high value, which is larger than comparison voltage VR corresponding to the theoretical air/fuel ratio.

As a result, at the rich air/fuel ratio, differential amplifier 39 provides from its output terminal pumping voltage Vp having a lower value (1.0V, for example) than that (1.5V, for example) of virtual ground 35 on the side of inner electrodes 28, 29.

On the other hand, when the air/fuel ratio is in lean condition, output voltage Vs is lower than comparison voltage VR corresponding to the theoretical air/fuel ratio. Thus, differential amplifier 39 provides from its output terminal pumping voltage Vp having a higher value (2.0V, for example) than that (1.5V, for example) of virtual ground 35 on the side of inner electrodes 28, 29.

In such a way, differential amplifier 39 can provide pumping voltage Vp having a value increased or decreased greatly in accordance with whether the air/fuel ratio is in rich condition or in lean condition. Pumping voltage Vp has a characteristic switched between low and high values with respect to virtual ground 35 on the side of inner electrodes 28, 29.

As a result, the direction of pumping current Ip which flows between inner electrode 28 and outer measuring electrode 30 through solid electrolyte layer 27, for example, can be switched in accordance with whether the air/fuel ratio is in rich condition or in lean condition. This pumping current Ip can be taken as an air/fuel-ratio signal from detection terminals 40, 41 as shown in FIG. 7, for example.

At the rich air/fuel ratio, outer measuring electrode 30 is lower in potential than inner electrode 28, so that electrochemical decomposition reaction given by the following reaction formula (III) is produced at outer measuring electrode 30 (cathode). This adds electrons to carbon-dioxide molecules which remain in exhaust gas, for example, generating oxygen ions and carbon monoxide.

$$CO_2 + 2e \rightarrow O^{2-} + CO \tag{III}$$

where $CO_2$ is carbon-dioxide molecule, e is electron, $O_{2-}$ is oxygen ion, and CO is carbon-monoxide molecule.

Then, oxygen ions are transported from outer measuring electrode 30 (cathode) to inner electrode 28 (anode) through oxygen deficiency in solid electrolyte layer 27. Moreover, electrochemical decomposition reaction given by the following reaction formula (IV) is produced at inner electrode 28 (anode), so that carbon-monoxide molecules in exhaust gas led to inner electrode 28 through gas diffusion layer 26 are bonded to oxygen ions, and thus decomposed into carbon dioxide and electrons:

$$CO + O^{2-} \rightarrow CO_2 + 2e \tag{IV}$$

where CO is carbon-monoxide molecule, $O^{2-}$ is oxygen ion, $CO_2$ is carbon-dioxide molecule, and e is electron.

When flammable-gas components in exhaust gas include hydrogen, electrochemical decomposition reaction given by the following reaction formula (V) is produced at outer measuring electrode 30. This adds electrons to water molecules which remain in exhaust gas to generate oxygen ions and hydrogen.

$$H_2O + e \rightarrow O^{2-} + H_2 \tag{V}$$

where $H_2O$ is water molecule, e is electron, $O^{2-}$ is oxygen ion, and $H_2$ is hydrogen molecule.

Then, oxygen ions are transported from outer measuring electrode 30 (cathode) to inner electrode 29 (anode) through oxygen deficiency in solid electrolyte layer 27. Moreover, electrochemical decomposition reaction given by the following reaction formula (VI) is produced at inner electrode 28 (anode), so that hydrogen molecules in exhaust gas are bonded to oxygen ions, and thus decomposed into water molecules and electrons:

$$H_2 + O^{2-} \rightarrow H_2O + 2e \tag{VI}$$

where $H_2$ is hydrogen molecule, $O^{2-}$ is oxygen ion, $H_2O$ is water molecule, and e is electron.

In such a way, at the rich air/fuel ratio, oxygen ions are transported from outer measuring electrode 30 (cathode) to inner electrode 28 (anode), so that control is carried out to decrease a difference in oxygen partial pressure between inner electrodes 28, 29 and reference electrode 31. That is, control is carried out to switch determination on the air/fuel ratio in accordance with the voltage of reference electrode 31, i.e. output voltage Vs, from rich determination to lean determination.

On the other hand, at the lean air/fuel ratio, outer measuring electrode 30 is higher in potential than inner electrode 28, so that electrochemical decomposition reaction given by reaction formula (I) is produced at inner electrode 28 (cathode). This adds electrons to oxygen molecules in exhaust gas led to inner electrode 28 through gas diffusion layer 26, generating oxygen ions.

Then, oxygen ions are transported from inner electrode 28 to outer measuring electrode 30 through oxygen deficiency in solid electrolyte layer 27. As a result, electrochemical decomposition reaction given by reaction formula (II) is produced at outer measuring electrode 30 to decompose oxygen ions into oxygen and electrons.

In such a way, at the lean air/fuel ratio, oxygen ions are transported from inner electrode 28 (cathode) to outer measuring electrode 30 (anode), so that control is carried out to increase a difference in oxygen partial pressure between inner electrodes 28, 29 and reference electrode 31. That is, control is carried out to switch determination on the air/fuel ratio in accordance with the voltage of reference electrode 31, i.e. output voltage Vs, from lean determination to rich determination.

As a result, the direction of pumping current Ip which flows between inner electrode 28 and reference electrode 31 is switched in accordance with whether the air/fuel ratio is in rich condition or in lean condition, providing linear change with respect to the theoretical air/fuel ratio. This pumping current Ip is detected as voltage across detection terminals 40, 41 having therebetween detection resistance Rp as shown in FIG. 7, which can be taken as an air/fuel-ratio detection signal.

It is noted that when compact layer 32 for restraining entry of exhaust gas conceals reference electrode 31, but not outer measuring electrode 30, gas diffusion layer 26, and the like to have roughly the whole circumference exposed to outside, a plurality of paths run in various directions, which allow exhaust gas to reach inner electrodes 28, 29 through the gas diffusion layer 28.

This raises easy occurrence of variations in gas diffusion resistance produced when exhaust gas reaches electrodes 28, 29 through gas diffusion layer 26. Thus, as shown by a characteristic curve in FIG. 9, pumping current Ip does not provide a flat characteristic and exhibits hysteresis, achieving difficultly a stable characteristic, resulting in possible reduction in detection accuracy of the air/fuel ratio.

Then, in this embodiment, gas introduction window 33 with predetermined opening width W is formed in compact layer 32 arranged to externally conceal gas diffusion layer 26, outer measuring electrode 30, and reference electrode 31. Gas introduction window 33 allows entry of outside exhaust gas toward gas diffusion layer 26 and outer measuring electrode 30 in the range of opening window W.

Gas introduction window 33 is shaped like a rectangular opening by cutting in a C-shape an end of compact layer 32 to partly expose an end of gas diffusion layer 26 together with solid electrolyte layer 27 and outer measuring electrode 30 to outside as shown in FIGS. 2 and 3.

Thus, with air/fuel-ratio detecting element 21 of roughly circular rod-like shape as a whole, rectangular gas introduction window 33 with opening width W of, e.g. $\frac{2}{3} \times D$, where D is outer diameter of compact layer 32, can be formed in compact layer 32. With this, the direction or path of outside exhaust gas entering gas diffusion layer 26 can be limited to substantially one direction within the range of opening width W, e.g. direction of arrow A in FIG. 5.

As a result, the gas diffusion distance required for exhaust gas to travel from gas diffusion layer 26 to inner electrodes 28, 29 along the direction of arrow A in FIG. 5 can be maintained roughly constant, resulting in favorable restraint of variations in gas diffusion resistance.

This can prevent variations in a diffusion limit value of pumping current Ip which flows between inner electrode 28 and outer measuring electrode 30, and thus pumping current Ip from being unstable as shown by characteristic curve 43 in FIG. 9. And this can provide flatness to a diffusion limit value of pumping current Ip with occurrence of hysteresis restrained.

Therefore, in this embodiment, the gas diffusion distance required for outside exhaust gas to travel from gas diffusion layer 26 to inner electrodes 28, 29 can be set roughly constant, stabilizing the characteristic of pumping current or diffusion limiting current Ip, resulting in enhanced detection accuracy of the air/fuel ratio.

Further, in this embodiment, heater pattern 24 is arranged on the outer peripheral surface of heater core 23 of small-diameter solid rod-like shape, and insulative heater covering layer 25 is arranged on the outer periphery of heater core in such a way as to externally envelop heater pattern 24, providing heater 22 of elongate rod-like shape.

Formed on the outer periphery of heater 22 through curved-surface printing or the like are gas diffusion layer 26, solid electrolyte layer 27, inner electrodes 28, 29, outer measuring electrode 30, reference electrode 31, compact layer 32, protecting layer 34, and the like.

As a result, air/fuel-ratio detecting element 21 of circular rod-like shape as a whole can be obtained, securing sufficient area for annular electrodes 28, 29, 30, 31 as compared with the plate-like air/fuel-ratio detecting element, resulting in a lowering of internal resistance and in a positive reduction in outer diameter, volume, and the like of air/fuel-ratio detecting element 21.

Further, the outside shape of air/fuel-ratio detecting element 21 can be of a circular rod with no edge portion as compared with that of the plate-like air/fuel-ratio detecting element with edge portions, achieving a reduction in thermal stress and the like of air/fuel-ratio detecting element 21, resulting in restrained occurrence of cracking or the like in solid electrolyte layer 27, for example.

Still further, air/fuel-ratio detecting element 21 can be manufactured by successively curved-surface printing heater pattern 24, heater covering layer 25, gas diffusion layer 26, inner electrodes 28, 29, solid electrolyte layer 27, outer measuring electrode 30, reference electrode 31, compact layer 32, and protecting layer 34 on the outer periphery of heater core 23, leading to great enhancement in workability of air/fuel-ratio detecting element 21.

Furthermore, heater 22 has outer periphery concealed with gas diffusion layer 26, solid electrolyte layer 27, compact layer 32, and the like. This can restrain heater 22 from coming into direct contact with outside air to reduce an influence of the outside-air temperature, and can increase a heating area of heater 22 to effectively transfer heat of heater 22 to solid electrolyte layer 27 and the like.

With this, a temperature-rise time of heater 22 can surely be shortened, resulting not only in shortened activation time of solid electrolyte layer 27, but also in earlier detection of the oxygen concentration or the like in exhaust gas even at engine start and thus immediate feedback control of the fuel injection amount. Moreover, the degree of mouthing flexibility can be enlarged, leading to a reduction in power consumption of heater 22.

Further, there is no need to form a particular reference air chamber or the like in air/fuel-ratio detecting element 21 so as to introduce air therein, allowing simplification of the structure thereof, resulting in enhancement in workability of air/fuel-ratio detecting element 21.

Still further, solid electrolyte layer 27 is held between inner electrode 28 and outer measuring electrode 30 and between inner electrode 29 and reference electrode 31. That is, the use of only one coat of solid electrolyte layer 27 allows construction of a so-called pumping cell, Nernst cell, and the like, achieving a reduction in outer diameter of air/fuel-ratio detecting element 21 in its entirety, resulting in downsizing of the apparatus.

Referring to FIG. 10, there is shown second embodiment of the present invention which is substantially the same as the first embodiment except that a compact layer or second compact layer 52 is arranged between lead portion or wire 29A of inner electrode 29 and lead portion or wire 31A of reference electrode 31 to restrain entry of gas to be measured.

Referring to FIG. 10, in the second embodiment, the air/fuel-ratio detecting apparatus comprises an air/fuel-ratio detecting element 51 which is of substantially the same structure as air/fuel-ratio detecting element 21 described in the first embodiment, and comprises heater 22, gas diffusion layer 26, solid electrolyte layer 27, inner electrodes 28, 29, outer measuring electrode 31, compact layer 32, gas introduction window 33, protecting layer 34, and the like.

However, air/fuel-ratio detecting element 51 differs from air/fuel-ratio detecting element 21 in that compact layer 52 as will be described later is between lead portion 29A of inner electrode 29 and lead portion 31A of reference electrode 31.

In the second embodiment, compact layer 52 is arranged aside from compact layer 32, and is formed out of substantially the same material as that of compact layer 32 as described in the first embodiment to prevent entry of outside exhaust gas.

After curved-surface printing solid electrolyte layer 27 on the outer periphery of gas diffusion layer 26 and before curved-surface printing outer measuring electrode 30 and reference electrode 31 thereon, compact layer 52 is formed, for example, on the outer periphery of heater covering layer 25 through curved-surface printing or the like. Compact layer 52 cooperates with heater covering layer 25 to envelop lead portion 29A of inner electrode 29 roughly throughout its length.

After printing of compact layer 52, outer measuring electrode 30 and reference electrode 31 are curved-surface printed on the outer periphery of solid electrolyte layer 27, and have respective lead portions formed through printing to extend in the axial direction of air/fuel-ratio detecting element 51 along compact layer 52. And compact layer 32 is formed thereon as described in the first embodiment.

Thus, the unillustrated lead portion of outer measuring electrode 30 and lead portion 31A of reference electrode 31 are held between compact layers 52, 32, by which outside exhaust gas or exhaust gas which passes through gas diffusion layer 26 is prevented from contacting lead portion 31A of reference electrode 31.

Therefore, the second embodiment can produce substantially the same effect as that of the first embodiment. Particularly, since the second embodiment is such that additional compact layer 52 is arranged between lead portion 29A of inner electrode 29 and lead portion 31A of reference electrode 31, lead portion 31A of reference electrode 31 is isolated from lead portion 29A of inner electrodes 28, 29, and thus can more surely be prevented from contacting exhaust gas. This allows, for example, restraint of oxygen accumulated in reference electrode 31 from leaking to gas diffusion layer 26, leading to a positive reduction in leakage amount of oxygen.

As a result, the oxygen partial pressure of reference electrode 31 can be maintained roughly constant as reference oxygen partial pressure, achieving stable sensor output. And voltage Vo of DC power source 38 externally applied thereto can be reduced to a lower value, leading to enhancement in energy efficiency.

According to the present invention, the opening formed in the compact layer can restrict paths of outside gas entering the gas diffusion layer and the second electrode in the range of the width of the opening, allowing the gas to reach the first electrode through the gas diffusion layer along roughly one direction.

As a result, the gas diffusion distance required for the gas to travel from the gas diffusion layer to the first electrode can be maintained roughly constant, preventing variations in a diffusion limit value of the pumping current which flows between the first and second electrodes, and thus pumping current from being unstable. This can enhance not only flatness of the pumping current or diffusion limiting current with occurrence of hysteresis restrained, but also detection accuracy of the air/fuel ratio with the characteristic of the pumping current as an air/fuel-ratio signal stabilized.

Further, according to the present invention, when the air/fuel-ratio detecting apparatus is shaped like a roughly circular rod as a whole, the rectangular opening having width of, e.g. (⅔ to 1)×D, where D is outer diameter of the first compact layer, can be formed in the first compact layer. This can restrict paths of the gas entering the gas diffusion layer in the range of the width of the opening and along roughly one direction, e.g. axial direction of the air/fuel-ratio detecting apparatus. This also can favorably restrain occurrence of variations in gas diffusion resistance when the gas reaches the first electrode through the gas diffusion layer.

Still further, according to the present invention, the lead wire of the third electrode is isolated from the lead wire of the first electrode, and thus can more surely be prevented from contacting the gas, allowing the oxygen partial pressure of the third electrode to be maintained roughly constant as reference oxygen partial pressure. This can achieve stable sensor output, and reduce the voltage externally applied thereto to a lower value, leading to enhancement in energy efficiency.

Furthermore, according to the present invention, the gas diffusion layer, the first electrode, the solid electrolyte layer, the second and third electrodes, and the first compact layer can successively be formed on the outer periphery of the heater of elongate rod-like shape in a laminated way through curved-surface printing or the like, achieving the air/fuel-ratio detecting apparatus of circular rod-like shape as a whole. With this, the oxygen concentration or the like in the gas can be detected with stable accuracy without being affected by the direction of mounting, the direction of flow of the gas, and the like.

Moreover, the first electrode and the second and third electrodes can be disposed to radially face each other across the solid electrolyte layer, achieving increased electrode area and decreased electrode-to-electrode distance, resulting in a reduction in electrical resistance. Further, there is no need to introduce reference air into the air/fuel-ratio detecting element, achieving simplified structure of the air/fuel-ratio detecting apparatus, resulting in enhancement of workability of the air/fuel-ratio detecting apparatus. Moreover, the heater is in the form of a stem, and the gas diffusion layer, the solid electrolyte layer, the first, second and third electrodes, and the first compact layer are formed on the outer periphery thereof, allowing an increase in heating area of the heater with respect to the solid electrolyte layer even when the heater is of a smaller diameter, leading to efficient transfer of heat of the heater to the solid electrolyte layer and the like.

Having described the present invention in connection with the illustrative embodiments, it is noted that the present invention is not limited thereto, and various changes and modifications can be made without departing from the scope of the present invention.

By way of example, in the illustrative embodiments, inner electrodes or first electrodes 28, 29 are separated from each other in the axial direction of gas diffusion layer 26. Optionally, inner electrodes or first electrodes 28, 29 may be coupled integrally to form a single annular electrode which extends axially largely.

Further, one of two electrodes 28, 29, for example, inner electrode 29, may be cancelled to form the first electrode with inner electrode 28 only. In this variation, inner electrode 28 may be connected to virtual ground 35. It is noted that this variation produces substantially the same effect as that of the above embodiments.

The entire teachings of Japanese Patent Application P2002-333901 filed Nov. 18, 2002 are incorporated hereby by reference.

What is claimed is:

1. An apparatus for detecting an air/fuel ratio, comprising:
a heater which generates heat through outside energization;
a gas diffusion layer provided to the heater, the gas diffusion layer allowing a gas to be measured to diffuse therein;
a solid electrolyte layer provided to the heater outside the gas diffusion layer, the solid electrolyte layer being activated by heat of the heater, the solid electrolyte layer being oxygen-ion conductive;
a first electrode arranged between the gas diffusion layer and the solid electrolyte layer, the first electrode being exposed to the gas passing through the gas diffusion layer;
a second electrode arranged on an outer surface of the solid electrolyte layer, the second electrode facing the first electrode across the solid electrolyte layer, the second electrode and the first electrode allowing a pumping current to flow therebetween when externally applying voltage thereto;
a third electrode arranged on the outer surface of the solid electrolyte layer away from the second electrode, the third electrode and the first electrode allowing an electromotive force corresponding to an oxygen concentration in the gas to be generated therebetween;
a first compact layer arranged on the outer surface of the solid electrolyte layer, the first compact layer concealing externally the gas diffusion layer, the solid electrolyte layer, the second electrode, and the third electrode to restrain entry of the gas; and
an opening formed in the first compact layer, the opening having a predetermined width, the opening allowing entry of the gas toward the gas diffusion layer and the second electrode in a range of the width.

2. The apparatus as claimed in claim 1, wherein the opening is shaped like a rectangle by cutting an end of the first compact layer, the opening serving to partly expose the gas diffusion layer, the solid electrolyte layer, and the second electrode.

3. The apparatus as claimed in claim 2, wherein the width of the opening and an outer diameter of the first compact layer is in relationship given by W=($2/3$ to 1)×D, where W is the width of the opening, and D is the outer diameter of the first compact layer.

4. The apparatus as claimed in claim 2, wherein the opening is formed with a predetermined angle, the angle and the width being in relationship in connection with the outer diameter of the first compact layer, which is given by W=($\theta$/360)×D×$\pi$, where W is the width of the opening, $\theta$ is the angle, and D is the outer diameter of the first compact layer.

5. The apparatus as claimed in claim 1, further comprising lead wires provided to the first, second, and third electrodes, respectively, the lead wires extending in a length direction of the heater.

6. The apparatus as claimed in claim 5, further comprising a second compact layer arranged between the lead wire of the first electrode and the lead wire of the third electrode to restrain entry of the gas.

7. An apparatus for detecting an air/fuel ratio, comprising:
a heater which generates heat through outside energization;
a gas diffusion layer provided to the heater, the gas diffusion layer allowing a gas to be measured to diffuse therein;
a solid electrolyte layer provided to the heater outside the gas diffusion layer, the solid electrolyte layer being activated by heat of the heater, the solid electrolyte layer being oxygen-ion conductive;
a first electrode arranged between the gas diffusion layer and the solid electrolyte layer, the first electrode being exposed to the gas passing through the gas diffusion layer;
a second electrode arranged on an outer surface of the solid electrolyte layer, the second electrode facing the first electrode across the solid electrolyte layer, the second electrode and the first electrode allowing a pumping current to flow therebetween when externally applying voltage thereto;
a third electrode arranged on the outer surface of the solid electrolyte layer away from the second electrode, the third electrode and the first electrode allowing an electromotive force corresponding to an oxygen concentration in the gas to be generated therebetween;
a first compact layer arranged on the outer surface of the solid electrolyte layer, the first compact layer concealing externally the gas diffusion layer, the solid electrolyte layer, the second electrode, and the third electrode to restrain entry of the gas;
a second compact layer arranged between the lead wire of the first electrode and the lead wire of the third electrode to restrain entry of the gas; and
an opening formed in the first compact layer, the opening having a predetermined width, the opening allowing entry of the gas toward the gas diffusion layer and the second electrode in a range of the width.

8. An apparatus for detecting an air/fuel ratio, comprising:
a heater which generates heat through outside energization, the heater being shaped like an elongate rod;
a gas diffusion layer arranged on an outer periphery of the heater, the gas diffusion layer allowing a gas to be measured to diffuse therein;
a solid electrolyte layer arranged on an outer periphery of the gas diffusion layer, the solid electrolyte layer being activated by heat of the heater, the solid electrolyte layer being oxygen-ion conductive;

a first electrode arranged on an inner periphery of the solid electrolyte layer, the first electrode being located between the gas diffusion layer and the solid electrolyte layer;

a second electrode arranged on an outer periphery of the solid electrolyte layer, the second electrode and the first electrode allowing a pumping current to flow therebetween when externally applying voltage thereto;

a third electrode arranged on the outer periphery of the solid electrolyte layer away from the second electrode, the third electrode and the first electrode allowing an electromotive force corresponding to an oxygen concentration in the gas to be generated therebetween;

a first compact layer arranged on the outer periphery of the solid electrolyte layer, the first compact layer concealing externally the gas diffusion layer, the solid electrolyte layer, the second electrode, and the third electrode to restrain entry of the gas; and an opening formed in the first compact layer, the opening having a predetermined width, the opening allowing entry of the gas toward the gas diffusion layer and the second electrode in a range of the width.

9. The apparatus as claimed in claim 8, wherein the opening is shaped like a rectangle by cutting an end of the first compact layer, the opening serving to partly expose the gas diffusion layer, the solid electrolyte layer, and the second electrode.

10. The apparatus as claimed in claim 9, wherein the width of the opening and an outer diameter of the first compact layer is in relationship given by $W=(\frac{2}{3} \text{ to } 1) \times D$, where W is the width of the opening, and D is the outer diameter of the first compact layer.

11. The apparatus as claimed in claim 9, wherein the opening is formed with a predetermined angle, the angle and the width being in relationship in connection with the outer diameter of the first compact layer, which is given by $W=(\theta/360) \times D \times \pi$, where W is the width of the opening, $\theta$ is the angle, and D is the outer diameter of the first compact layer.

12. The apparatus as claimed in claim 8, further comprising lead wires provided to the first, second, and third electrodes, respectively, the lead wires extending in a length direction of the heater.

13. The apparatus as claimed in claim 12, further comprising a second compact layer arranged between the lead wire of the first electrode and the lead wire of the third electrode to restrain entry of the gas.

* * * * *